(12) United States Patent
Beyer et al.

(10) Patent No.: US 6,670,469 B1
(45) Date of Patent: Dec. 30, 2003

(54) METHOD FOR PRODUCING REGULAR POROUS CELLULOSE PEARLS, CORRESPONDING CELLULOSE PEARLS AND USE THEREOF

(75) Inventors: Christine Beyer, Rudolstadt (DE); Frank Meister, Rudolstadt (DE); Christoph Michels, Rudolstadt (DE); Bernd Riedel, Dorfkulm (DE); Eberhard Taeger, WeiBbach (DE)

(73) Assignee: Thuringisches Institut fur Textil-und Kunststoff-Forschung E.V., Rudolstadt (DE)

( * ) Notice: Subject to any disclaimer, the term of this patent is extended or adjusted under 35 U.S.C. 154(b) by 0 days.

(21) Appl. No.: 09/367,404

(22) PCT Filed: Dec. 9, 1998

(86) PCT No.: PCT/DE98/03657

§ 371 (c)(1),
(2), (4) Date: Aug. 12, 1999

(87) PCT Pub. No.: WO99/31141

PCT Pub. Date: Jun. 24, 1999

(30) Foreign Application Priority Data

Dec. 14, 1997 (DE) ......................... 197 55 353
Dec. 14, 1997 (DE) ......................... 197 55 352

(51) Int. Cl.$^7$ ............................ C08B 37/00; C07H 1/00
(52) U.S. Cl. ............................... 536/56; 536/124
(58) Field of Search ............................. 536/56, 124

(56) References Cited

U.S. PATENT DOCUMENTS

| | | | | | |
|---|---|---|---|---|---|
| 4,063,017 A | * | 12/1977 | Tsao et al. | ...................... | 536/57 |
| 4,461,892 A | * | 7/1984 | Nishikawa et al. | ............ | 536/65 |
| 4,958,014 A | * | 9/1990 | Shirokaze | ...................... | 536/56 |
| 5,047,180 A | * | 9/1991 | Steiner et al. | .................. | 264/5 |
| 5,196,527 A | * | 3/1993 | Ookuma et al. | ............... | 536/56 |
| 5,607,695 A | * | 3/1997 | Ek et al. | ...................... | 424/468 |

* cited by examiner

Primary Examiner—James O. Wilson
Assistant Examiner—Everett White
(74) Attorney, Agent, or Firm—Howard M. Ellis

(57) ABSTRACT

Process for producing regular porous pearl cellulose with a particle size in the range from 2 to 1,000 µm, comprising the steps:

a) a cellulose having a degree of polymerisation in the range from 150 to 2,000 is dissolved in a solvent to form a solution of 0.5 to 25% by mass, b) the cellulose solution is finely divided and dispersed in a dispersant which is immiscible with said solution and has a viscosity in the range from 10 to 80,000 mPa·s, c) the dispersed solution particles are solidified to regular pearl particles by precipitating with a liquid precipitating agent miscible with the solvent (1) after cooling the dispersion to below the melting temperature of the cellulose solution and separating the frozen particles of the cellulose solution from the dispersant or (2) directly in the dispersion, and d) the pearl particles are separated from the liquid mixture of solvent, precipitating agent and possibly dispersant.

25 Claims, No Drawings

METHOD FOR PRODUCING REGULAR POROUS CELLULOSE PEARLS, CORRESPONDING CELLULOSE PEARLS AND USE THEREOF

The invention is concerned with a process for producing regular porous pearl celluloses having a particle size in the range from 2 to 1,000 μm. Furthermore, the invention is concerned with a pearl cellulose with specific properties as well as the use of the pearl cellulose with specific properties as well as the use of the pearl celluloses produced according to the process of the invention.

Regular porous pearly celluloses are a relatively inexpensive, stable material with variably adjustable chemical properties compared with other separator and carier materials. To an increasing extent cellulosic molded articles are gaining significence as chromatographic material, carriers for enzymes, cells and other ligands, e.g. after activation and coupling of proteins.

The known processes for producing such molded cellulose articles differ substantially from each other by the type of the cellulose material used, the solvent used, the manner of coagulation or regeneration, as well as the technology of division.

Thus, the patent rights JP 48-2173, JP 48-60753, JP 62-191033, Cs 172 640, U.S. Pat. No. 2,543,928, DE 2 005 408, etc., specify the use of alkaline solutions of cellulose xanthate (viscose) which are either sprayed into an acid precipitating bath or regenerated by an acid or thermal decomposition after having been dispersed in a solvent immiscible with water. A disadvantage of the procedure is that a considerable danger potential for the environment is associated with the sulfur compounds released with the regeneration, the resulting dilute acids and salt solutions and by the used organic solvents, respectively.

Other processes, e.g. according to DD 259 533, propose the use of solutions of cellulose carbamate. A specific disadvantage of this process is the necessity of an expensive after-treatment in which urea must be removed with hot water and residual carbamate groups must be decomposed with soda lye.

According to a further group of protective rights one of them from highly substituted organo-soluble cellulose esters among which cellulose acetate with an average substitution degree (DS) between 2 and 3 is preferably used. The principle of these processes passing via pearls of cellulose acetate as an intermediate results in that cellulose acetate is preferably dissolved in a halogenated hydrocarbon, the polymer solution is dispersed and solidified by vaporisation of the solvent. After separating the cellulose acetate particles the acetate groups are usually split off by a treatment with sodium hydroxide solution, e.g. JP 53-7759. As with this procedure only particles with a low porosity are obtained, many processes have been proposed which aim at a higher porosity of the resulting molded cellulose bodies. The chosen method is the addition of various pore forming agents to the cellulose acetate solution. The patents JP 56-24429, JP 24430, JP 62-267339, JP 63-68645 and U.S. Pat. No. 4,312,980 propose the use of linear alcohols. Motozato et al, J. Chromatogr. 298 (3), (1984) 499–507 prefer for this purpose hydrocarbons, such as hexane, cyclohexane, petroleum ether, toluene and similar compounds. Furthermore the patent JP 63-68645 proposes the use of long-chain carboxylic acids or esters of carboxylic acids for this aim. With all of these modifications the disadvantage is the necessity to use toxic halogenated hydrocarbons as the solvent.

The process of the patents SU 931 727 and SU 1 031 966 the subject of which is the production of cellulose pearls from cellulose acetate with a DS of 2 from a mixture of ethylacetate and n-butanol allows no adjustment of porosities of <75%. The proposed use of oleic acid requires additional washing processes with use of volatile organic solvents.

A procedure for producing pearly cellulose particles with use of cellulose silylethers as specified in the patent DD 295 861 also uses volatile hydrocarbons or toxic halogen hydrocarbons as the solvent. With the acid or alkaline regeneration substantial amounts of silyl side groups remain behind on the cellulose which groups substantially restrict the use for chromatographic and medical purposes.

Up to now for the direct cellulose dissolution solvents have been proposed which are difficult to handle. Thus, the patents DE 1 792 230, FR 1 575 419, U.S. Pat. No. 3,597,350 specify the use of cuoxam and similar compounds.

The protective right JP 80-44312 and Kuga, J. Chromatogr. 195, (1980), 221–230 propose working in melts of CaSCN.

Furthermore, in JP 82-159802 mixtures of dimethylsulfoxide and paraformaldehyde are specified as solvents. Especially the multi-component solvents cause substantial problems when introducing celluloses of higher molecular weight in amounts above 5%. In addition these solvent mixtures can be recycled only to a very restricted extent.

With regard to dispersing the polymer solution after having left the nozzle in principle three technologies have been specified. The patents U.S. Pat. No. 5,047,180 and U.S. Pat. No. 5,328,603 teach the production of spherical molded pieces by spraying (atomizing) a polymer solution. In the last of said patents the multicomponent solvent dimethylacetamide/LiCl is used as a solvent for cellulose. Such a system requires salt additions of more than 10% for the manufacture of regular particles. The EP 0 268 866 realizes the division into polymer droplets by superposition of the longitudinal motion of the polymer solution exiting from the nozzle by a rotating vibration motion. Finally in DE 44 24 998 spherical particles are produced by dividing a polymer solution exiting from the nozzle by means of extremely thin rotating cutters. All the process variants are identical in that an irreversible coagulation step follows directly after dividing the polymer solution. With this it is necessary that the polymer particles adopt the regular shape when passing a more or less short distance of falling. This results in problems with forming an ideal spherical shape by premature hardening, deformations as a result of the impact on the surrounding collecting cylinder and possibly gluey coatings on the cutters so that more or less distinct variations of the shape must be accepted.

It is an object of the invention to provide a process for producing regular porous cellulose pearls which is technically simple and economical and allows the production of pearl bodies having a defined particle diameter with a narrow particle size distribution in the overall range from 2 to 1,000 μm and with a broad range of variation of the adjustable porosities. Especially the process should allow to produce cellulose pearls with particle sizes in the partial range from 2 to 50 μm or in the partial range from 40 to 1,000 μm. With this process salt-free solvents, particularly one-component solvents are to be used which are little toxic or non-toxic. A further object is to provide a process in which the indicated drawbacks of the known processes are avoided. Finally it is the object of the invention to provide a new pearly cellulose with new applications. Further advantages can be gathered from the following specification.

With the process mentioned at the beginning these objects are achieved according to the invention in that a) a cellulose having a degree of polymerisation in the range from 150 to 2,000 is dissolved in a solvent to form a solution of 0.5 to 25% by mass cellulose, b) the cellulose solution is finely divided and dispersed in a dispersant which is not miscible with said solution and has a viscosity in the range from 10 to 80,000 mpa·s, c) the dispersed solution particles are solidified to regular pearl particles by precipitating with a liquid precipitating agent miscible with the solvent
   1) after cooling the dispersion to below the melting temperature of the cellulose solution and separating the frozen particles of the cellulose solution from the dispersant or
   2) directly in the dispersion, and d) the pearl particles are separated from the liquid mixture of solvent, precipitating agent and possibly dispersant.

step a) may include other than cellulose particles at least one inert solid introduced in an amount ranging from 5 to 200% by weight relative to the cellulose present. The inert solid can be a powdery material with particle size diameters ranging from 50 to 3,000 μm. More specifically, the inert powdery material, other than cellulose, may have particle size diameters of greater than 40 μm. The particles may be polysaccharides or inorganic compounds.

Step b) can be performed with a volume ratio of cellulose solution to dispersant in a range from 1:1 to 1:20.

with a preferred embodiment of the process for preparing pearly celluloses with a particle size in the range from 2 to 50 μm the solution with 0.5 to 15% by mass cellulose is dispersed directly in a liquid inert medium, and the dispersion is further processed by the procedure of the steps c) and d). It has been found that the separation of the steps of forming and solidification by converting the cellulose dispersion after lowering the temperature into a suspension results in substantial simplifications of the production process.

With another preferred embodiment of the process of the invention for preparing pearl celluloses with a particle size ranging from 50 to 1,000 um the cellulose solution is shaped in the step b) by pressure to form at least one strand with a diameter in the range from 40 to 1,000 um, the solution strand is divided by rotating cutter jets into defined sections, and these solution particles are collected in the dispersant and maintained in motion. The separation of the process steps of dividing, forming and solidifying results in a simple manner in highly regular pearl cellulose of a narrow particle size distribution and in variably adjustable pore volumes and allows a substantial simplification of the production process.

Further embodiments of the process of the invention are defined by separating the phases of the suspension, the inert medium for division or dispersion which is immiscible with water, can be recycled directly, i.e. without additional purifying steps, such as extraction etc., into the process cycle and can be reused for the shaping process, possibly after having added auxiliary agents for enhancing the dispersing procedure.

The frozen polymer droplets separated by filtration or centrifugation can be advantageously solidified in a precipitating bath with maintenance of the properties achieved in the shaping step. The separated mixture of solvent and precipitating agent can be separated e.g. by use of thermal energy or by membranes so that the onecomponent-solvent can advantageously circulate in a short cycle.

The concentration of the cellulose solution can be adjusted within broad limits as a function of the desired particle size or pore volumes whereby solutions with a cellulose concentration from 0.5 to 15, preferably 1 to 12 and especially 2 to 7% by mass are suitable for producing the regular porous cellulose of the invention having particle diameters from 2 to 50 μm and 50 to 1,000 μm, respectively.

The technique without a rotating cutter used with the production of pearly cellulose in the size range from 50 to 1,000 μm minimizes the danger of glueing the cutting tools with polymer droplets and additionally attributes to the high particle uniformity. For equalizing the particles and forming homogeneous particle sizes it is helpful to maintain the division during and/or after the introduction of the cellulose droplets in the dispersing medium until a stable suspension is formed by the precipitation and reduction of temperature, respectively.

When forming particles in the range from 2 to 50 μm viscosity gradients between the cellulose solution and the dispersion medium are utilized. For equalizing the particles and forming small particle sizes rapidly rotating dispersing devices, for example of the type Ultra-Turrax with a speed in the range from 1,000 to 10,000 $min^{-1}$ with intensively acting dispersing tools, for example with a cutter-mixer-head or with dispersing bars, are used during and/or after charging the dispersing medium with the cellulose solution. Subsequently the division/dispersion can be maintained until a stable suspension is formed by lowering the temperature.

The possibly frozen polymer droplets are separated by filtration or centrifugation and then supplied to a precipitating bath in which they are solidified. After having separated the obtained regular porous cellulose pearls from the precipitating bath by filtration or centrifugation a washing or purification step with water or lower alcohols is carried out in the temperature range from 3 to 90° C.

Conveniently emulsifiers such as non-ionic surfactants from the group of polyoxyethylene alkylether, polyoxyethylene arylalkyl-ether or polyoxyethylene sorbitan alkylether, are added to the inert division or dispersion medium.

The pearls celluloses can be subsequently activated and possibly coupled with various ligands via spacers. If necessary they are dried. The pearl celluloses of the invention are characterized by a particle size range from 50 to 1,000 μm, a pore volume from 5 to 95% and an exclusion limit $\leq 5 \times 10^6$ Dalton, or they are characterized by a particle size range from 2 to 50 um, a pore volume <50% and an exclusion limit $\leq 5 \times 10^4$ Dalton. These properties can be adjusted within narrow tolerances in the specified ranges by the process of the invention and the respective embodiments of the process. The pore volume indicates the portion of a cellulose sphere which is characterized by more or less big voids. The pore volume can be determined by electron microscopy of different sections of the cellulose sphere, by Hg-porosimetry or with a known dependency by the water retention—CRC-value (DIN 53814).

The pearl celluloses of the invention, especially those with a particle size ranging from 2 to 50 μm, a pore volume of less than 50% and an exclusion limit of $\leq 5 \times 10^4$ Dalton can advantageously be used for example as separating agent and carrier agent for chromato-graphic and diagnostic purposes, e.g. for diagnostic agents and bio-catalysts, as selective or specific adsorbent with the detoxification of blood and as a cell culture carrier in biotechnology, biomedicine and medicine. The pearl cellulose is particularly useful as a matrix for the gel filtration chromatography (GFC) by which molecules, mainly macromolecules are separated on the basis of the pore diameter and the exclusion limit, respectively.

The exclusion limit characterizes the limit of the magnitude of a void (pore) up to which a molecule can penetrate into this void, even only partially. It represents therefore the greatest possible dimension of a molecule for which a chromatographic separation is still possible. The exclusion limit is determined by measuring the permeation of known substances with a defined molecular size. In the present case the exclusion limits are determined by the permeation of high-molecular Dextran Blue (compare J. Baldrian et al: "Small-angle scattering from macroporous polymers: styrene divinylbenzene copolymers, cellulose in bead form" in Coll. Chechoslov. Chem. Commun. 41 (1976) 12, p. 3555–3562). Particle size, pore volume and exclusion limit are always used in their entirety by producers and users in order to characterize the different products and to compare them.

The here-above used term "regular" means uniform in the sense of uniformity of the geometric shape. Ideally formed spheres allow an optimum packing density (hexagonally most closely packed structure). With chromatographic separation processes, good flow conditions for the phase to be separated and a good mechanical stability of the packing can be achieved with "regular" pearls or beads. As a result closely distributed separation curves are detected. The use of The invention will be explained by the following examples

EXAMPLE 1

In a round stopper flask 16.5 g wet-beaten cellulose with a cuoxam-dp of 482 and a water content of 60% and 1163 g of an aqueous solution containing 50% N-methylmorpholine-N-oxide (NMMO solution) were intensively agitated for 60 min. at 85° C. Subsequently 80 ml water were withdrawn with reduced pressure at a constant temperature and further agitation whereby a cellulose solution with 6% by mass cellulose was formed. The polymer solution was dispersed at 75° C. in 200 g paraffin oil (viscosity>110 mPa·s) to which 2.5 g Tween® 80 (polyoxyethylene lauryl ether, product of ICI) was added, with use of an Ultra-Turrax with a cutting-mixing head tool at 9,000 revolutions/min. In order to maintain the dispersion further agitation was carried out with an agitator at 250 revolutions/min. with cooling down to 35° C. whereby the polymer droplets froze. The obtained suspension was separated by centrifugation, and the frozen polymer droplets were transferred at room temperature into an aqueous precipitating bath containing 70% isopropanol. The separated dispersant was reused for the dispersing step. The cellulose beads had an average particle size of 25 $\mu$m and a pore volume of approximately 40%.

EXAMPLE 2

7.5 g wet-beaten cellulose with a cuoxam-dp of 1,634 and 168.2 g of an aqueous 50% NMMO solution were filled into an round stopper flask. 76 ml water were withdrawn from the mixture under vacuum at 85° C. whereby a solution of 3% cellulose was formed. For producing the pearl cellulose the procedure is the same as in Example 1. The obtained cellulose beads had an average particle diameter of 15 $\mu$m, a pore volume of 47% and an exclusion limit of $2\times10^3$ Dalton.

EXAMPLE 3

7.5 g wet-beaten cellulose were introduced into 168.2 g aqueous 50% NMMO solution in a round stopper flask in which previously 1.0 g ZnO was distributed with intensive agitation. The cellulose was the same as in Example 1. The mixture was agitated for 60 min. at 85° C. 76 ml water were withdrawn under vacuum so that a solution of approx. 3% cellulose was formed. The polymer solution was dispersed by means of am Ultra-Turrax at 10,000 revolutions/min. at 75° C. in 200 g silicone oil (viscosity 53 mpa·s) to which 3 g Brij® 35 were added. After 15 minutes the Ultra-Turrax was turned off and the resulting dispersion was cooled down to 25° C. with agitation at 250 revolutions/min. After separation of the frozen polymer droplets by centrifugation and subsequent precipitation in an aqueous bath cellulose beads having an average particle diameter of 10 $\mu$m and a pore volume of 8% were obtained. The surface of the molded pieces was characterized by a small porosity.

EXAMPLE 4

11 g microcrystalline cellulose having a cuoxam-dp of 150 and a residual moisture content of 12% were introduced into 90 g NMMO monohydrate and homogeneously dissolved at 90° C. with agitation. The polymer solution war dispersed in 200 g paraffin oil with a viscosity of >110 mPa·s at 20° C. which contains 2.5 g Tween® 85 (polyoxyethylene sorbitan trioleat), at 80° C. by means of an Ultra-Turrax and dispersion tool at 9,500 $min^{-1}$. After 25 min. the Ultra-Turrax was turned off, and the resulting dispersion was subsequently agitated at 250 $min^{-1}$ with cooling. The dispersion was slowly agitated for 35 minutes at 35° C., and the frozen polymer droplets were centrifugated and for their solidification introduced into an aqueous precipitating bath after adding 70% isopropanol. The obtained pearl cellulose had an average particle diameter of 5 $\mu$m and a pore volume of 10%.

EXAMPLE 5

4 g dry-milled pulp with a cuoxam-dp of 1,634 were slowly introduced with agitation at room temperature into 196 g trifluoroacetic acid (98%, Bp=72° C.). The pulp was dissolved with slow agitation at 25° C. in a round stopper flask with reflux condenser. After 2 h the mixture was heated to 50° C. and was agitated for a further 30 minutes in order to complete the dissolution. Then it was again cooled to room temperature. The cellulose solution was dispersed at 25° C. with an Ultra-Turrax and dispersing tool at 9,500 revolutions/min. in 200 g paraffin oil containing 2.5 g Tween® 85 and having a viscosity of 25 to 50 mPa·s at 20° C. The Ultra-Turrax was switched off after 25 min. and the resulting dispersion was stirred at 250 revolutions/min. with cooling down to –200° C. The frozen polymer droplets were centrifuged at this temperature and introduced into an alcoholic bath containing isopropanol and tert-butanol in a ratio by volume of 50/50 for the precipitation. The obtained cellulose beads had an average particle diameter of 10 $\mu$m and a pore volume of 10%.

EXAMPLE 6

12.5 wet-beaten cellulose having a cuoxam-dp of 1,634 and a water content of 60% and 252 g aqueous 50% NMMO solution were intensively stirred at 85° C. in a round stopper flask. Subsequently 85 g water were distilled off under reduced pressure and with agitation, and 50 g anhydrous dimethyl sulfoxide were added. For completing the dissolution a further 30 g water were distilled off so that a 2.5% solution of cellulose was formed.

The polymer solution was pressed at 70° C. through a nozzle hole having a diameter of 50 $\mu$m. The ejected solution strand was divided by a rotating liquid jet of paraffin oil under a pressure of 100 bar to regular cylindrical sections having a height of about 45 $\mu$m.

The solution particles dropping down in the extruding direction were caught in a cylindrical vessel containing a dispersion medium of 300 g paraffin oil to which 1 g Brij® 35 (polyoxyethylene laurylether, non-ionic emulsifier of ICI) was added. The cylindrical sections were formed to solution droplets at a temperature of 75° C. with slow agitation (200 min$^{-1}$). The droplets were frozen to regular solid particles after reducing the temperature to 10° C. The solid particles were filtered off from the dispersion medium and were subsequently solidified in an aqueous precipitation bath containing 50% by mass dimethyl sulfoxide. The obtained pearl cellulose had an average particle diameter of 55 μm±10% and a pore volume of about 65%.

EXAMPLE 7

25 g cellulose having a degree of polymerisation (dp) of 482 and a residual moisture of 60% were intensively mixed at 85° C. with 163 g 50% NMMO solution and 5 g polyethylene glycol having a molecular weight of 35,000. 80 ml water were withdrawn from the mixture under reduced pressure and agitation at a constant temperature so that a fine-disperse emulsion from cellulose solution and polyethylene glycol was formed. The emulsion was pressed through a nozzle hole having a diameter of 50 μm without a further retention time. The extruded strand was divided into sections in the same manner as in example 6. The sections were caught in polyalkylsiloxane which had a viscosity of 50 Pa·s and comprised 2.5 g emulsifier (Brij® 35). The formed polymer droplets were precipitated in the dispersion cooled down to 50° C. with slow stirring, by adding 1,500 g deionized water. The polyethylene glycol left in the cellulose beads was completely removed by extraction with hot water so that regular particles with a diameter of 60 μm and a pore volume of 83% were obtained.

EXAMPLE 8

15 g cellulose as in example 6 were mixed with 163 g 50% NMMO solution at 80° C. and dissolved by withdrawing 80 ml water with reduced pressure 50 g ε-caprolactam were subsequently added to the cellulose solution at the same temperature, and the mixture was stirred until a homogeneous mass was formed. The polymer solution was pressed at 75° C. through a nozzle hole having a diameter of 100 μm and divided into cylindrical polymer sections in the same manner as in example 6. The polymer droplets formed after slow agitation were caused to freeze by lowering the temperature of the dispersion to 35° C.; the solid was filtered off and precipitated in a bath containing 50% ε-caprolactam and 50% isopropanol. The cellulose pearls had a particle diameter of 150 μm and a pore volume of 87%.

EXAMPLE 9

The same procedure as in the example 6 was followed with the exception that cellulose having a dp of 532 was used. The obtained cellulose beads had the same particle diameter and a pore volume of 70%.

EXAMPLE 10

The same procedure as in the example 8 was followed. However, instead of caprolactam 2 g hydrolyzed pea starch having a molecular weight of 240,000 was worked into the polymer solution by pre-soaking the finely divided pea starch in the aqueous NMMO solution and subsequently introducing the wet-beaten cellulose. The obtained cellulose pearls had an average particle diameter of 175 μm and a pore volume of 80% with mostly mesopores and macropores being formed.

EXAMPLE 11

4 g dry-milled linters gulp having a dp of 1,634 were fed at room temperature into 96 g trifluoroacetic acid (98%, BP=72° C.) being in a round stopper flask equipped with an agitator and a reflux condenser, and the mixture was stirred for 2 h at 25° C. In order to complete the dissolution the mixture was heated to 50° C. and stirred for further 30 minutes. After being cooled to room temperature the solution was divided in the same manner as in example 6 and further stirred at 250 min$^{-1}$ with cooling to −20° C. The frozen polymer droplets were centrifuged off at this temperature and were brought into an alcoholic bath containing isopropanol and tert-butanol in a volume ratio 50/50 for the precipitation. The pearly cellulose had an average particle diameter of 60 μm and a pore volume of 10%.

What is claimed is:

1. A process for producing porous pearl cellulose particles of substantially uniform geometric shape and particle size having a diameter ranging from about 2 to 1000 μm, which comprises the steps of:
    a) forming a 0.5 to 25% by weight cellulose solution by dissolving cellulose in a solvent, said cellulose having a degree of polymerization in a range from 150 to 2,000;
    b) dispersing the cellulose solution in a dispersant which is immiscible with said cellulose solution to form a dispersion of finely divided cellulose particles with a viscosity in a range from 10 to 80,000 mPas, said dispersion formed by pressure to at least one strand, dividing the solution strand into defined sections with rotating cutting jets, and catching and maintaining in motion the dispersed particles in said dispersant, wherein said dispersion is performed at a temperature range from 60 to 100° C.;
    c) solidifying the dispersed finely divided cellulose particles to pearl particles having substantially uniform geometric shape by precipitating with a liquid precipitating agent miscible with said solvent;
        i) by cooling said dispersion to below the melting temperature of the cellulose solution and separating frozen articles of the cellulose from said dispersant, wherein said cooling is performed at a temperature in the range of about 0–60° C., or
        ii) by precipitating with a liquid precipitating agent miscible with said solvent directly in the dispersion, and
    d) separating the pearl particles from said solvent and precipitating agent, and dispersant, when present.

2. The process according to claim 1 wherein the diameter of the pearl cellulose particles produced is in a range from 2 to 50 μm and the dispersant is directly introduced into the cellulose solution which comprises from 0.5 to 15% by weight cellulose and the if dispersion is processed according to said steps c(i) and d).

3. The process according to claim 2 wherein step b) is performed under action of a shearing field of a dispersing to rotating at a speed ranging from $10^3$ to $10^4$ revolutions/min.

4. The process according to claim 2 wherein step b) is performed with a volume ratio of cellulose solution to dispersant in a range from 1:1 to 1:20.

5. The process according to claim 1 wherein the diameter of the pearl cellulose particles produced is in the range of 50 to 1,000 μm and the dispersion of step b) is formed by pressure to at least one strand having a diameter in a range from 40 to 1,000 μm.

6. The process according to claim 5 wherein the cellulose solution is extruded through at least one nozzle and the cutting jets are generated by a compressed inert liquid.

7. The process according to claim 5 wherein the dispersion in step b) is slowly mixed with an agitator.

8. The process according to claim 1 wherein said solvent is miscible with water, said dispersant is anhydrous and immiscible with water, and said precipitating agent consists at least partially of water.

9. The process according to claim 1 wherein said solvent is salt-free and/or the precipitating agent is an aqueous salt solution.

10. The process according to claim 1 wherein the solution of step a) includes other than cellulose particles at least one inert solid introduced in an amount ranging from 5 to 200% by weight relative to cellulose present.

11. The process according to claim 10 wherein the particles other than cellulose have diameters of less than 40 $\mu$m and the particles are polysaccharides or inorganic compounds.

12. The process according to claim 11 wherein the polysaccharides or inorganic compounds are selected from the group consisting of starch, xanthane, galactomannanes and zinc oxide.

13. The process according to claim 1 wherein the solution of step a) including other than cellulose a powdery material with particle size diameters ranging from 50 to 3,000 nm.

14. The process according to claim 1 wherein the dispersant is a member selected from the group consisting of polyalkysiloxanes, paraffins and polypropylene glycols.

15. The process according to claim 1 wherein step b) is performed by the addition of at least one emulsifier in an amount ranging from 1 to 30% by weight based on cellulose.

16. The process according to claim 15 wherein the emulsifier is a nonionic surfactant selected from the group consisting of polyoxyalkylene alkylether, polyoxyethylene arylalkylether and polyoxyethylene sorbitanalkylether.

17. The process according to claim 1 wherein separating the particles in step c(i) is carried out by filtration or centrifugation.

18. The process according to claim 1 wherein precipitating in step c) is carried out with at least one precipitating agent selected from the group consisting of water, lower alcohols and polyols with a molecular weight of less than 600.

19. The process according to claim 1 wherein the solvent in step a) is a one-component solvent selected from the group consisting of a tertiary amine oxide, preferably N-methylmorpholine-N-oxide monohydrate, or trifluoroacetic acid.

20. The process according to claim 1 wherein the cellulose solution of step a) is formed with a cellulose content in a range from 1 to 15% by weight.

21. The process according to claim 1 wherein step a) is performed with cellulose having a degree of polymerization in a range from 200 to 1,500.

22. The process according to claim 1 wherein said dispersant of step (b) possesses a viscosity in a range from 15 to $5 \times 10^4$ mPa·s.

23. The process according to claim 1 wherein said dispersant is recovered in step c(i) or from the mixture of step d) and recycled for use in step b).

24. The process according to claim 1 wherein the solvent and precipitating agent in step d) are separated and the solvent recycled for use in step a) and the precipitating agent recycled for use in step c).

25. The process according to claim 1 wherein cooling in step c(i) is carried out with agitation.

\* \* \* \* \*